(12) United States Patent
Elia et al.

(10) Patent No.: US 9,820,915 B2
(45) Date of Patent: Nov. 21, 2017

(54) NASO/OROGASTRIC TUBE HAVING ONE OR MORE BACKFLOW BLOCKING ELEMENTS, BACKFLOW BLOCKING ELEMENTS, AND A METHOD OF USING BACKFLOW BLOCKING ELEMENTS

(75) Inventors: Liron Elia, Kiryat-Ata (IL); Gavriel J. Iddan, Haifa (IL); Nir Lilach, Kfar Yehoshua (IL); Eliahu Eliachar, Haifa (IL)

(73) Assignee: ART Healthcare Ltd., Natania (IL)

( * ) Notice: Subject to any disclaimer, the term of this patent is extended or adjusted under 35 U.S.C. 154(b) by 149 days.

(21) Appl. No.: 13/635,941

(22) PCT Filed: Jan. 27, 2011

(86) PCT No.: PCT/IL2011/000100
§ 371 (c)(1),
(2), (4) Date: Sep. 19, 2012

(87) PCT Pub. No.: WO2011/117853
PCT Pub. Date: Sep. 29, 2011

(65) Prior Publication Data
US 2013/0012920 A1    Jan. 10, 2013

Related U.S. Application Data

(60) Provisional application No. 61/340,622, filed on Mar. 22, 2010, provisional application No. 61/362,332, filed on Jul. 8, 2010.

(51) Int. Cl.
*A61J 15/00* (2006.01)
*A61M 25/04* (2006.01)
*A61M 1/00* (2006.01)

(52) U.S. Cl.
CPC ....... *A61J 15/0003* (2013.01); *A61J 15/0046* (2013.01); *A61M 1/008* (2013.01);
(Continued)

(58) Field of Classification Search
CPC .. A61J 15/0003; A61J 15/0026; A61J 15/003; A61J 15/0034; A61J 15/0046; A61J 15/008; A61J 15/0092
(Continued)

(56) References Cited

U.S. PATENT DOCUMENTS 3,483,859 A    12/1969 Pittman
3,565,079 A *  2/1971 Jackson ................... 128/207.15
(Continued)

FOREIGN PATENT DOCUMENTS

CN    1133471    10/1996
EP    0723216    7/1996
(Continued)

OTHER PUBLICATIONS

Communication Pursuant to Article 94(3) EPC dated Apr. 30, 2014 From the European Patent Office Re. Application No. 11706361.0.
(Continued)

*Primary Examiner* — Bhisma Mehta
*Assistant Examiner* — Nilay Shah

(57) ABSTRACT

A naso/orogastric device that comprises a naso/orogastric tube sized and shaped for being disposed within the esophagus so that at least a distal segment thereof being placed in the stomach lumen of a patient and at least one self expending element disposed around a peripheral surface of the naso/orogastric tube and having a first thickness in a compressed state and a second thickness in an expanded state, the at least one self expending element switching from the compressed state to the expanded state when absorbing moisture. The first thickness is thinner than the second thickness.

17 Claims, 13 Drawing Sheets

(52) U.S. Cl.
CPC .......... *A61M 25/04* (2013.01); *A61J 15/0076* (2015.05); *A61M 1/0031* (2013.01); *A61M 2210/105* (2013.01); *A61M 2210/1053* (2013.01)

(58) Field of Classification Search
USPC ....... 604/514, 516, 104, 270, 910, 317, 326, 604/327, 328
See application file for complete search history.

(56) References Cited

U.S. PATENT DOCUMENTS

| | | | |
|---|---|---|---|
| 3,731,691 A * | 5/1973 | Chen .................. | A61M 16/044 128/207.15 |
| 4,340,046 A | 7/1982 | Cox | |
| 4,384,584 A * | 5/1983 | Chen ............................... | 604/28 |
| 4,393,873 A | 7/1983 | Nawash et al. | |
| 4,417,576 A | 11/1983 | Baran | |
| 4,543,089 A * | 9/1985 | Moss ............................... | 604/43 |
| 4,752,286 A * | 6/1988 | Okada ............................ | 604/506 |
| 4,840,173 A | 6/1989 | Porter, III | |
| 5,027,812 A * | 7/1991 | Shapiro et al. .......... | 128/207.18 |
| 5,067,497 A | 11/1991 | Greear et al. | |
| 5,100,384 A | 3/1992 | McBrien et al. | |
| 5,314,409 A | 5/1994 | Sarosiek et al. | |
| 5,370,656 A | 12/1994 | Shevel | |
| 5,458,568 A * | 10/1995 | Racchini et al. ............... | 604/19 |
| 5,638,813 A | 6/1997 | Augustine | |
| 5,937,861 A | 8/1999 | Augustine | |
| 5,997,503 A * | 12/1999 | Willis et al. .............. | 604/103.07 |
| 6,277,113 B1 | 8/2001 | Berube | |
| 2001/0053920 A1 | 12/2001 | Shaker | |
| 2002/0111386 A1 | 8/2002 | Sekins et al. | |
| 2004/0034320 A1* | 2/2004 | Burnett ............... | A61J 15/0015 604/96.01 |
| 2004/0220534 A1* | 11/2004 | Martens .................. | A61L 29/16 604/265 |
| 2005/0059965 A1 | 3/2005 | Eberl et al. | |
| 2007/0044807 A1* | 3/2007 | Madsen ............ | A61M 16/0479 128/207.15 |
| 2007/0282307 A1 | 12/2007 | Holte | |
| 2008/0023005 A1* | 1/2008 | Tokunaga ......... | A61M 16/0463 128/205.19 |
| 2008/0033415 A1 | 2/2008 | Rieker et al. | |
| 2008/0097179 A1 | 4/2008 | Russo | |
| 2008/0154191 A1 | 6/2008 | Gobel | |
| 2008/0167607 A1 | 7/2008 | Pfeiffer et al. | |
| 2009/0032027 A1 | 2/2009 | McCachren et al. | |
| 2009/0062725 A1 | 3/2009 | Goebel | |
| 2009/0187187 A1 | 7/2009 | Asirvatham et al. | |
| 2010/0249639 A1 | 9/2010 | Bhatt | |
| 2013/0014761 A1 | 1/2013 | Elia et al. | |
| 2013/0158514 A1 | 6/2013 | Elia et al. | |
| 2016/0113843 A1 | 4/2016 | Elia et al. | |

FOREIGN PATENT DOCUMENTS

| | | |
|---|---|---|
| JP | 2006-525089 | 11/2006 |
| JP | 2007-500060 | 1/2007 |
| JP | 2008-511362 | 4/2008 |
| JP | 2009-505721 | 2/2009 |
| WO | WO 2004/096330 | 11/2004 |
| WO | WO 2004/105833 | 12/2004 |
| WO | WO 2005/046759 | 5/2005 |
| WO | WO 2006/024825 | 3/2006 |
| WO | WO 2007/024288 | 3/2007 |
| WO | WO 2007095541 A2 * | 8/2007 |
| WO | WO 2008/107872 | 9/2008 |
| WO | WO 2008107872 A2 * | 9/2008 |
| WO | WO 2008/154450 | 12/2008 |
| WO | WO 2009/027864 | 3/2009 |
| WO | WO 2009/141598 | 11/2009 |
| WO | WO 2010/016054 | 2/2010 |
| WO | WO 2011/117854 | 9/2011 |

OTHER PUBLICATIONS

Notification of Office Action dated Jul. 30, 2014 From the State Intellectual Property Office of the People's Republic of China Re. Application No. 201180025103.8 and Its Translation Into English.
Search Report dated Jul. 30, 2014 From the State Intellectual Property Office of the People's Republic of China Re. Application No. 201180025103.8 and Its Translation Into English.
International Preliminary Report on Patentability dated Oct. 4, 2012 From the International Bureau of WIPO Re. Application No. PCT/IL2011/000100.
International Preliminary Report on Patentability dated Oct. 4, 2012 From the International Bureau of WIPO Re. Application No. PCT/IL2011/000101.
Communication Relating to the Results of the Partial International Search dated Jun. 6, 2011 From the International Searching Authority Re. PCT/IL2011/000101.
International Preliminary Report on Patentability dated Aug. 9, 2012 From the International Bureau of WIPO Re. Application No. PCT/IL2011/000099.
International Search Report and the Written Opinion dated May 18, 2011 From the International Searching Authority Re. Application No. PCT/IL2011/000100.
International Search Report and the Written Opinion dated Jun. 21, 2011 From the International Searching Authority Re. Application No. PCT/IL2011/000099.
International Search Report and the Written Opinion dated Sep. 30, 2011 From the International Searching Authority Re. Application No. PCT/IL2011/000101.
Notice of Reason for Rejection dated Dec. 2, 2014 From the Japanese Patent Office Re. Application No. 2013-500648 and Its Translation Into English.
Applicant-Initiated Interview Summary dated Jan. 21, 2015 From the US Patent and Trademark Office Re. U.S Appl. No. 13/575,974.
Notice of Reason for Rejection dated Jan. 6, 2015 From the Japanese Patent Office Re. Application No. 2012-550569 and Its Translation Into English.
Communication Under Rule 164(2)(a) EPC dated Mar. 23, 2015 From the European Patent Office Re. Application No. 11706933.6.
Notification of Office Action and Search Report dated Mar. 11, 2015 From the State Intellectual Property Office of the People's Republic of China Re. Application No. 201180025103.8 and Its Translation Into English.
Official Action dated Apr. 20, 2015 From the US Patent and Trademark Office Re. U.S. Appl. No. 13/575,974.
Patent Examination Report dated Mar. 6, 2015 From the Australian Government, IP Australia Re. Application No. 2011210363.
Patent Examination Report dated Mar. 12, 2015 From the Australian Government, IP Australia Re. Application No. 2011231096.
Notification of Office Action and Search Report dated May 22, 2015 From the State Intellectual Property Office of the People's Republic of China Re. Application No. 201180017052.4 and Its Translation Into English.
Advisory Action and Interview summary dated Aug. 6, 2015 From the US Patent and Trademark Office Re. U.S. Appl. No. 13/575,974.
Applicant-Initiated Interview Summary dated Jul. 21, 2015 From the US Patent and Trademark Office Re. U.S. Appl. No. 13/575,974.
Communication Pursuant to Article 94(3) EPC dated Jun. 15, 2015 From the European Patent Office Re. Application No. 11706361.0.
Communication Pursuant to Article 94(3) EPC dated Jul. 29, 2015 From the European Patent Office Re. Application No. 11706933.6.
Restriction Official Action dated Sep. 21, 2015 From the US Patent and Trademark Office Re. U.S. Appl. No. 13/635,949.
Notification of Office Action dated Nov. 2, 2015 From the State Intellectual Property Office of the People's Republic of China Re. Application No. 201180025103.8.
Notification of Office Action dated Nov. 12, 2015 From the State Intellectual Property Office of the People's Republic of China Re. Application No. 201180017052.4 and Its Translation Into English.
Translation Dated Nov. 17, 2015 of Notification of Office Action dated Nov. 2, 2015 From the State Intellectual Property Office of the People's Republic of China Re. Application No. 201180025103.8.

(56) References Cited

OTHER PUBLICATIONS

Official Action dated Dec. 15, 2015 From the US Patent and Trademark Office Re. U.S. Appl. No. 13/635,949.
Decision of Rejection dated Dec. 1, 2015 From the Japanese Patent Office Re. Application No. 2013-500648 and Its Translation Into English.
Notification of Office Action dated Oct. 15, 2014 From The State Intellectual Property Office of the People's Republic of China Re. Application No. 2011800170524 and Its Translation Into English.
Official Action dated Oct. 21, 2014 From the US Patent and Trademark Office Re. U.S. Appl. No. 13/575,974.
Search Report dated Oct. 15, 2014 From the State Intellectual Property Office of the People's Republic of China Re. Application No. 2011800170524 and Its Translation Into English.
Communication Pursuant to Article 94(3) EPC dated Dec. 1, 2014 From the European Patent Office Re. Application No. 11706361.0.
Official Action dated Jun. 3, 2016 From the US Patent and Trademark Office Re. U.S. Appl. No. 13/635,949.
Communication Pursuant to Article 94(3) EPC dated Feb. 21, 2017 From the European Patent Office Re. Application No. 11706934.4. (7 Pages)
Requisition by the Examiner dated Jan. 25, 2017 From the Canadian Intellectual Property Office Re. Application No. 2,793,853. (8 Pages).
Official Action dated Dec. 15, 2016 From the US Patent and Trademark Office Re. U.S. Appl. No. 13/635,949. (26 pages).

\* cited by examiner

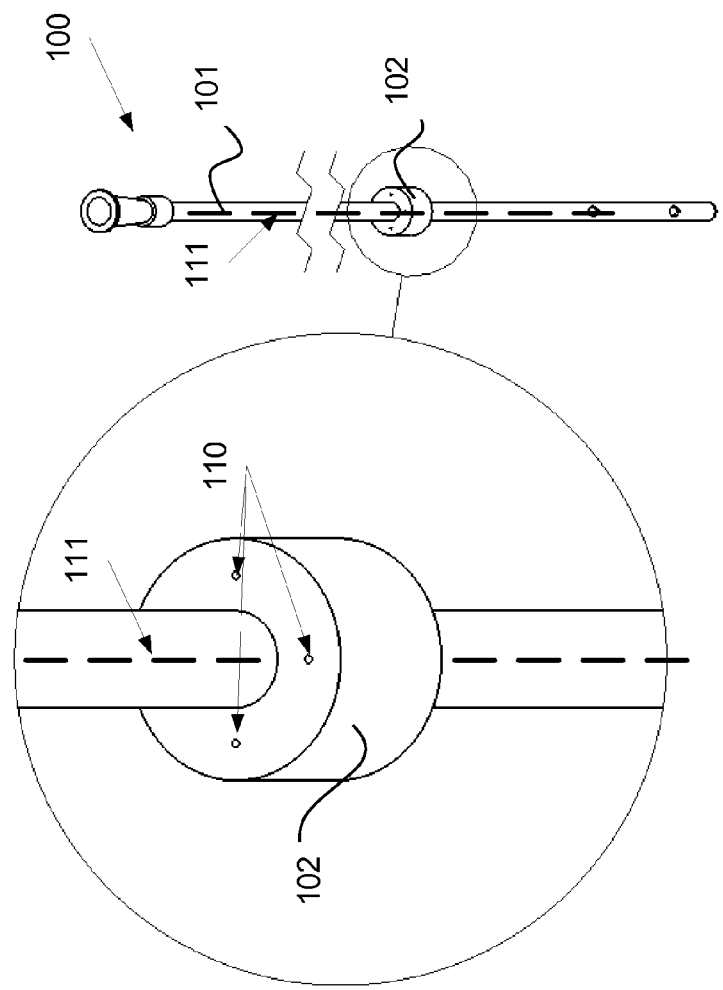
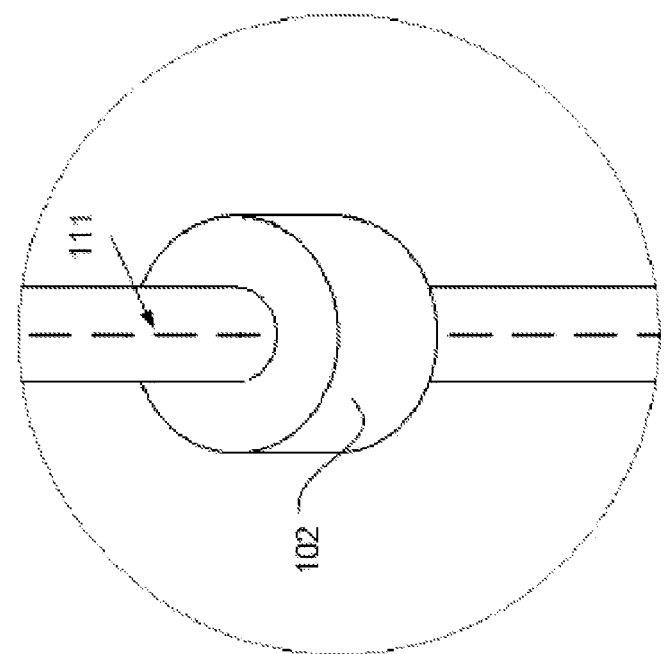
FIG. 1A  FIG. 1B  FIG. 1C

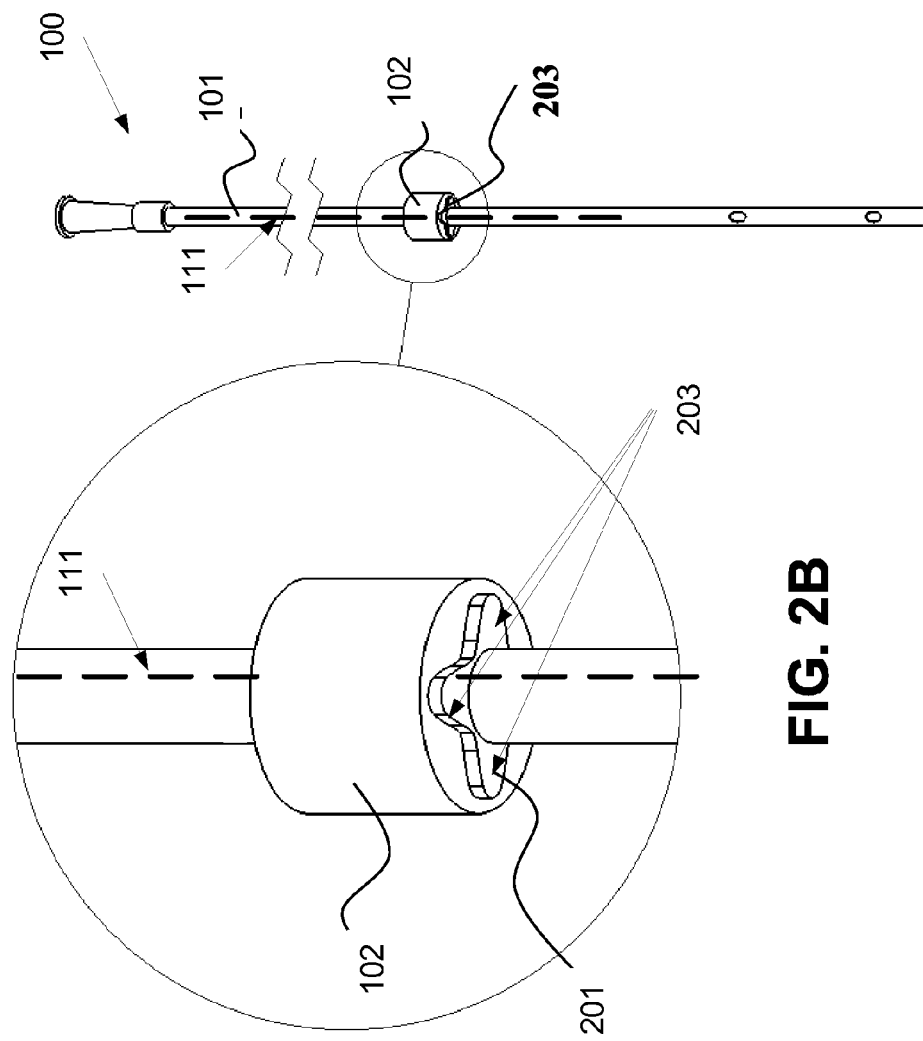

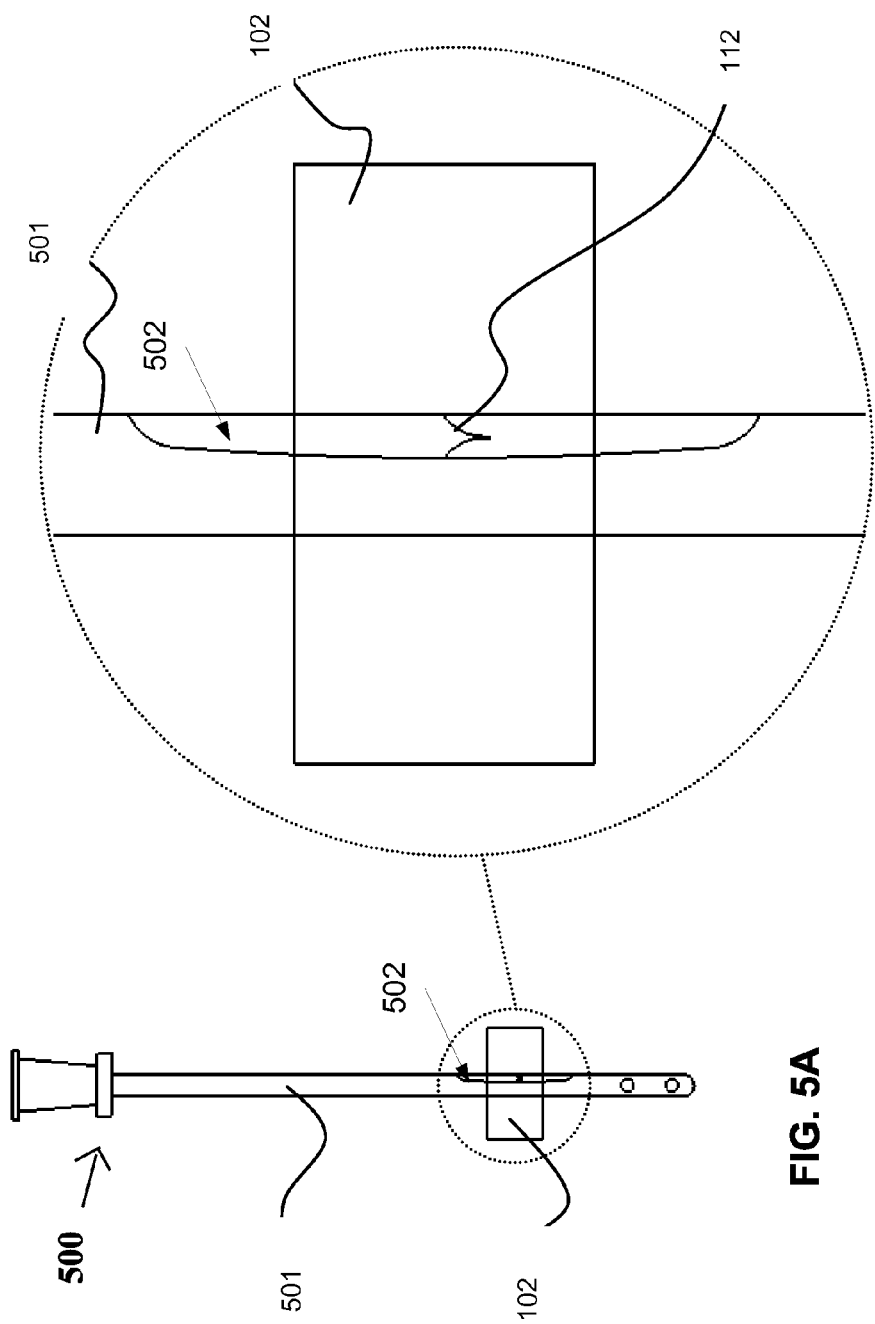

NASO/OROGASTRIC TUBE HAVING ONE OR MORE BACKFLOW BLOCKING ELEMENTS, BACKFLOW BLOCKING ELEMENTS, AND A METHOD OF USING BACKFLOW BLOCKING ELEMENTS

RELATED APPLICATIONS

This application is a National Phase of PCT Patent Application No. PCT/IL2011/000100 having International filing date of Jan. 27, 2011, which claims the benefit of priority under 35 USC §119(e) of U.S. Provisional Patent Application Nos. 61/340,622 filed on Mar. 22, 2010 and 61/362,332 filed on Jul. 8, 2010. The contents of the above applications are all incorporated by reference as if fully set forth herein in their entirety.

FIELD AND BACKGROUND OF THE INVENTION

The present invention, in some embodiments thereof, relates to tubes which are used for delivering fluids into the body via natural openings, such as naso/orogastric tubes and, more particularly, but not exclusively, to a naso/orogastric tube having backflow blocking elements and a method of using and producing thereof.

Naso/orogastric feeding, such as nasogastric or nasoenteral tubes (short-term use) or Gastrostomy and jejunostomy tube (long-term use) is a form of alimentation and/or metabolic support in which nutrient formulas or medicaments are delivered directly to the gastrointestinal tract, either the stomach or the duodenum. In the majority of cases, nutrient administration is accomplished through use of a tube based device or system, delivering the nutrient through the patient's pharynx and esophagus directly into the stomach, the duodenum or small intestinum. One of the difficulties of esophageal feeding is the increased stimulation of reflux of gastroesophageal contents up the esophagus and pharynx and into the trachea of the patient.

A common preventive measure against reflux of gastroesophageal contents has been to elevate the patient's upper body into a semi-recumbent position, thereby reducing the ascension of gastric material up the esophagus.

A number of naso/orogastric tubes have been developed incorporating an esophageal balloon seal against gastroesophageal contents ascending from the stomach into the pharynx. For example, U.S. Pat. No. 4,384,584, filed on Oct. 28, 1981 describes a naso-esophageal catheter is provided with an inflatable balloon at its distal end and a signal-emitting device is located within the balloon so that the location of the distal end of the catheter can be determined when it is advanced into the patient's esophagus. After the catheter has been advanced into the patient's esophagus, the balloon is inflated. Thereafter, an esophageal catheter is directed through the patient's neck towards the center of the inflated balloon. After the balloon has been punctured the naso-esophageal catheter is withdrawn and the patient can then be fed with liquid nutrients through the trans-cervical esophageal catheter.

Another example is described in U.S. Patent Application, Publication Number 2009/0062725, filed on Aug. 29, 2007 describes an enteral feeding unit that reduces the occurrence of gastroesophogeal-pharynegal reflux during feeding includes an automatable feeding pump with a feedback sensor for sensing a relative pressure in a patient's stomach and esophagus, and a regulator system for controlling and monitoring feeding rate to the patient as a function of the relative gastro-esophageal pressure. The system includes a stomach probe that provides a fluid-tight closure of the esophagus. The stomach probe includes a tampon-bladder for watertight closure of the esophagus, in which the tampon-bladder is formed of flexible and/or elastic material. At least an inner cavity of the bladder is provided for the reception of a fluid medium. A prescribed pressure for the medium in the tampon-bladder is maintained by an inner lumen forming the stomach probe, from which an outer hose-like lumen extending to the tampon bladder is so arranged that between the outer lumen and the inner lumen a channel is formed connected to the inner cavity of the tampon-bladder arranged on the outer lumen by a number of openings. The inner cavity of the tampon-bladder is connected via a canal formed between the inner and outer lumen with a suitably graded reservoir or equalizing vessel for the liquid medium situated above the tampon-bladder and outside the patient.

SUMMARY OF THE INVENTION

According to some embodiments of the present invention, there is provided a naso/orogastric device. The naso/orogastric device comprises a naso/orogastric tube sized and shaped for being disposed within the esophagus so that at least a distal segment thereof being placed in the stomach lumen of a patient and at least one self expanding element disposed around a peripheral surface of the naso/orogastric tube and having a first thickness in a compressed state and a second thickness in an expanded state, the at least one self expanding element switching from the compressed state to the expanded state when absorbing moisture. The first thickness is thinner than the second thickness.

Optionally, the at least one self expanding element having a disc shaped structure around the naso/orogastric tube when in the expanded state.

Optionally, the at least one self expanding element comprises at least one of compressed cellulose and Polyvinyl acetate (PVA).

Optionally, the first thickness is at least ten folds thicker than the second thickness.

Optionally, the at least one self expanding element is at least partly soaked with a dissolvable material.

Optionally, the at least one self expanding element having at least one conduit for conducting biological fluids from the top of the at least one self expanding element to the bottom of the at least one self expanding element.

More optionally, the naso/orogastric device further comprises at least one conduit closing element having a closed state for substantially sealing the at least one conduit and an open state for substantially unsealing the at least one conduit.

More optionally, the at least one conduit closing element having at least one flap, each the flap being swingably coupled on a peripheral surface of the naso/orogastric tube so that the at least one flap swings relative to the naso/orogastric tube, the at least one flap swinging between the closed state and the open state.

Optionally, the naso/orogastric tube having at least one of a recess and a conduit for conducting biological fluids from the top of the at least one self expanding element to the bottom of the at least one self expanding element.

More optionally, the naso/orogastric device further comprises a unidirectional valve disposed in the lumen of the at least one of the recess and the conduit.

Optionally, the naso/orogastric device further comprises a suction unit for applying a suction force for drawing biological fluids accumulated above the at least one self expanding element.

More optionally, the suction unit having a plug for transmitting the suction force from an external source to a space above the at least one self expanding element, in proximity to the naso/orogastric tube.

More optionally, the suction unit having a mechanical valve for timing the applying, the mechanical valve being operated by the suction force.

More optionally, the naso/orogastric device further comprises at least one sensor for detecting at least one of a presence and an absence of biological fluids above the at least one self expanding element, in proximity to the naso/orogastric tube, the suction unit being operated according to at least one of the presence and the absence.

More optionally, the naso/orogastric device further comprises a suction timing unit for timing the operation of the suction unit.

More optionally, the naso/orogastric device further comprises the suction timing unit having a mechanic valve for timing the applying.

More optionally, the naso/orogastric device further comprises the suction timing unit having a solenoid based valve for timing the applying.

More optionally, the naso/orogastric device further comprises the timing is performed in every preset period.

More optionally, the naso/orogastric device further comprises a suction indication unit for indicating whether the suction force is applied.

Optionally, at least one self expanding element is circularly disposed around the peripheral surface.

More optionally, the naso/orogastric device further comprises a built in peristaltic pump for applying a suction force for drawing biological fluids accumulated above the at least one self expanding element.

According to some embodiments of the present invention, there is provided a method of at least one of performing a naso/orogastric procedure. The method comprises providing a naso/orogastric tube having an inner lumen at least one self expanding element disposed around a peripheral surface thereof, the at least one self expanding element having a first thickness in a compressed state and a second thickness in an expanded state, the at least one self expanding element switching from the compressed state to the expanded state when absorbing moisture, disposing the naso/orogastric tube within the esophagus so that a distal segment thereof being in an esophagus lumen of a patient, allowing the at least one self expanding element to absorb biological fluids so as to change from the compressed state to the expanded state in the esophagus lumen, and using the inner lumen for performing the naso/orogastric procedure.

Optionally, the naso/orogastric procedure is a member of a group consisting of a diagnostic procedure, a feeding procedure and a treatment of a stomach lumen.

According to some embodiments of the present invention, there is provided a backflow blocking element of a naso/orogastric tube. The backflow blocking element comprises a supporting member having an aperture sized for closely receiving a naso/orogastric tube and at least one self expanding element coupled to the supporting member so as to be circularly disposed around a peripheral surface of the naso/orogastric tube. The at least one self expanding element having a first thickness in a compressed state and a second thickness in an expanded state, the at least one self expanding element switching from the compressed state to the expanded state when absorbing moisture.

According to some embodiments of the present invention, there is provided a naso/orogastric device that comprises a naso/orogastric tube sized and shaped for being disposed within the esophagus so that at least a distal segment thereof being placed in the stomach lumen of a patient and at least one flexible and absorbent element each disposed around a peripheral surface of the naso/orogastric tube so as to project outwardly and extend the cross section area thereof.

Optionally, the at least one flexible and flexible and absorbent element changes thickness when absorbing moisture.

Optionally, the at least one flexible and flexible and absorbent element is made of spongy material.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1A is a schematic illustration of a distal tip of a naso/orogastric device having an self expanding element according to some embodiments of the present invention;

FIG. 1B is a blowup of the self expanding element of FIG. 1A, according to some embodiments of the present invention;

FIG. 1C is a blowup of the self expanding element of FIG. 1A where the self expanding element thereof have conduits, according to some embodiments of the present invention;

FIG. 2A is a schematic illustration of the naso/orogastric tube depicted in FIG. 1A with a conduit closing element, according to some embodiments of the present invention;

FIG. 2B is a blowup of the self expanding element with the conduit closing element as described in FIG. 2A, according to some embodiments of the present invention;

FIG. 5A is a schematic illustration of a naso/orogastric device having a naso/orogastric tube with one or more recesses, according to some embodiments of the present invention;

FIG. 5B is a blowup of an exemplary recess at the cross section of the backflow blocking element of the naso/orogastric device depicted in FIG. 5A, according to some embodiments of the present invention;

FIG. 10B is a blowup of the suction indication unit which is depicted in FIG. 10A, according to some embodiments of the present invention;

DESCRIPTION OF EMBODIMENTS OF THE INVENTION

Figure 1D:
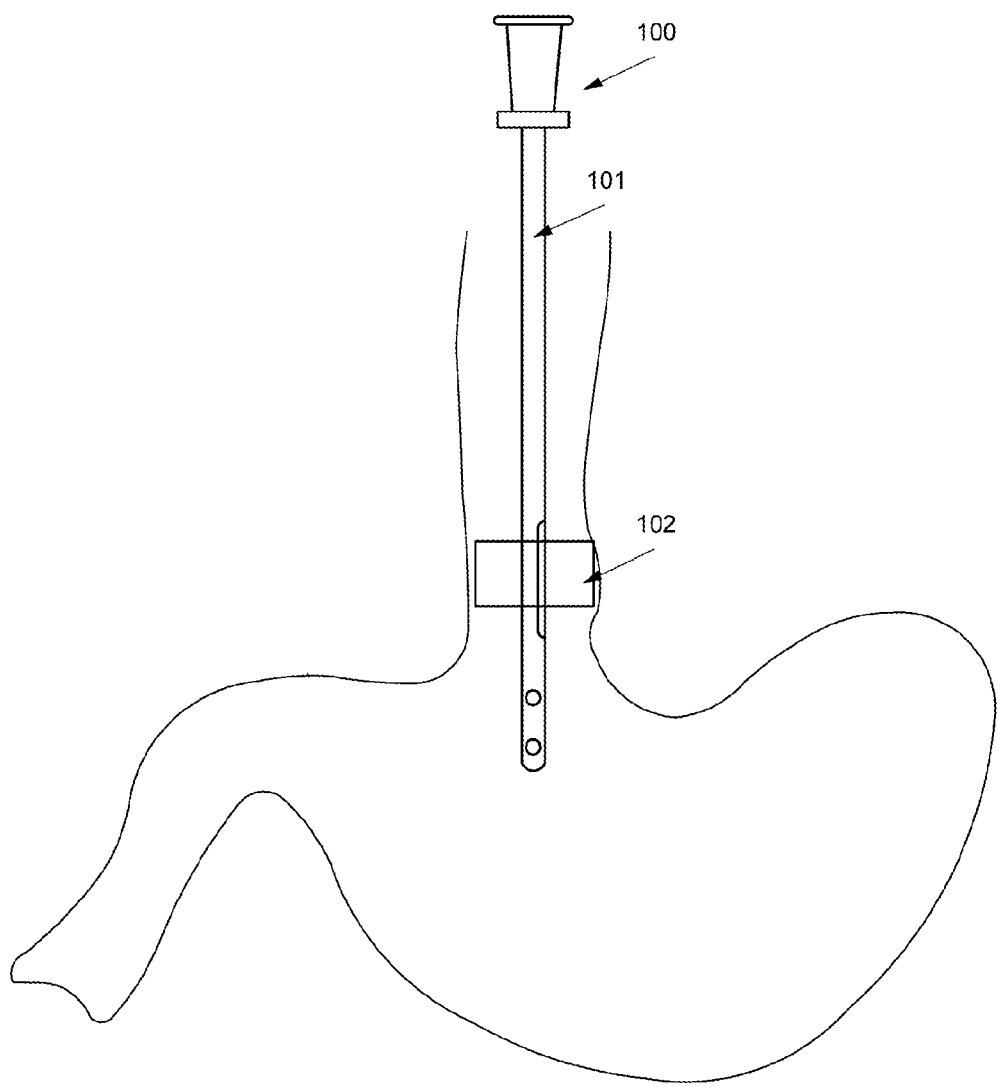
FIG. 1D is a schematic illustration of the naso/orogastric device depicted in FIG. 1A when being disposed in the esophagus, according to some embodiments of the present invention.

The present invention, in some embodiments thereof, relates to tubes which are used for delivering fluids into the body via natural openings, such as naso/orogastric tubes and, more particularly, but not exclusively, to a naso/orogastric tube having backflow blocking elements and a method of using and producing thereof.

According to some embodiments of the present invention there are provided methods and naso/orogastric devices, such as an esophageal feeding tube, a naso-esophageal catheter, a gastric feeding tube, such as a nasogastric feeding tube, a duodenal feeding tube and an enteral feeding tube, for blocking backflow of stomach contents during diagnosis, feeding and/or treatment of a patient via the esophagus using one or more self expanding elements, which are optionally expend when absorbing moisture. It should be noted that the term self expanding element is used to described herein any flexible and absorbent element, such as flexible and absorbent element made of a spongy material or any element that changes thickness when absorbing moisture. Optionally, the naso/orogastric device includes naso/orogastric tube sized and shaped for being disposed within the esophagus so that at least a distal segment thereof is placed in the stomach lumen of a patient. The device further includes one or more self expanding elements disposed around, optionally a peripheral surface of the naso/orogastric tube and having a compressed state and an expanded state. The self expanding elements optionally switches from the compressed state to the expanded state when absorbing biological fluids, such as saliva and blood or can already be disposed expended in body lumen, such as the esophagus. The thickness in an expanded state is thicker than in a compressed state so that the gap between the inner walls of the esophagus and the peripheral surface of the naso/orogastric tube at the respective cross section is sealed and/or substantially closed. The seal prevent from some or all of the backflow of stomach contents to move up along the esophagus. Optionally the backflow seal can be coated with bacteriostatic material for the prevention of infection in the esophagus. Optionally, one or more of the self expanding elements have conduits for facilitating the flowing of saliva and/or blood from the esophagus to the stomach. Optionally, one or more conduit closing elements are disposed in proximity to the conduits so as to prevent from backflow of stomach contents to move up, toward the pharynx, while allowing saliva and/or blood to move from the esophagus to the stomach. Additionally or alternatively, one or more recesses are formed in the naso/orogastric tube to facilitate the flowing of saliva and/or blood from the esophagus to the stomach via the cross section in which the self expanding elements are located. Optionally, a suction unit operated periodically and/or according to the reading of one or more sensors, is used for draining the saliva and/or blood from the esophagus.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Reference is now made to FIG. 1A, which is a schematic illustration of a distal tip of a naso/orogastric device 100 having an self expanding element 102 and to FIGS. 1B and 1C which are blowups of the self expanding element 102, according to some embodiments of the present invention.

The naso/orogastric device 100 includes a naso/orogastric tube 101 having an inner lumen for delivering nutrients, microorganisms, water and/or medications or for diagnostic purposes (probe). Optionally, the endotracheal tube is a naso/orogastric tube. The naso/orogastric tube 101 is defined herein as any commonly used naso/orogastric tube, for example an esophageal feeding tube, a naso-esophageal catheter, a gastric feeding tube, such as a nasogastric feeding tube, a duodenal feeding tube and an enteral feeding tube. The naso/orogastric tube 101 may be used for guiding probes and/or sensors for GI diagnosis, for example imaging sensors. The naso/orogastric tube 101 is sized and shaped for being disposed within the esophagus so that a distal segment thereof is placed in the stomach lumen of a patient. Optionally, the naso/orogastric tube 101 comprises a small diameter flexible tube preferably made of transparent plastic, such as polyvinyl Chloride or silicone. The length of the naso/ orogastric tube 101 is adjusted to the size of the patient. For example, a naso/orogastric device for adult patients has a naso/orogastric tube 101 of more than 120 centimeter long for 18 Fr tube and a naso/orogastric device for infants has a naso/orogastric tube 101 of more than 40 centimeter long for 5 Fr tube.

The naso/orogastric device 100 further comprises one or more self expanding elements 102 placed to encircle, optionally substantially horizontality, an annular portion of the surface of the naso/orogastric tube 101, substantially perpendicularly to the main longitudinal axis 111 of the naso/orogastric tube 101. Each self expanding element 102 may include one or more segments which encircle, at least substantially, a cross section of the naso/orogastric tube 101. For example a number of segments may be disposed around a common plane one to the side of the other and/or in parallel planes, one above the other.

In use, the self expanding elements 102 are set to expand in the esophagus, blocking GI backflow from the stomach. The self expanding elements 102 has at least two states, a compressed state and an uncompressed expanded state. When the self expanding element(s) 102 are in a compressed state, the naso/orogastric device 100 may be guided via tubular lumens having a limited diameter, such as the esophagus, without applying damaging pressure on the inner walls. However, when the self expanding element(s) 102 are in an expanded state, their diameter increases and a flexibility is created for the tubular lumen.

Optionally, the self expanding element 102 is made of a biocompatible material such as crystal violet—a dye derived from gentian violet that is used as a general biological stain, an acid-base indicator, and an agent against infection by bacteria, fungi, pinworms, and other parasites. The biocompatible material is optionally porous, which expands when it absorbs biological fluids, for example the material is a spongy material, such as compressed cellulose and polyvinyl acetate (pva) or polyvinyl formal (pvf) that is manufactured from pva by reaction with butyraldehyde. Optionally, the self expanding element 102 is between about 0.2 mm thick and about 2 mm thick in a compressed state and about ten times thicker in an expanded state, for example when exposed to moist or biological fluids. Each self expanding element 102 is optionally shaped as a tube and coupled on a peripheral surface of the naso/orogastric tube 101 so that expands the diameter at a certain cross section thereof. In such an embodiment, the compressed state is achieved when the porous martial is in a non absorbed state and the expanded state is achieved when the porous martial is absorbed with biological fluids. The resulting shape of the self expanding element 102 in an expended state approximates a tube or a cylindrical roll, expanded in size with respect to its compressed, non-absorbed state. Optionally, the self expanding element 102 is comprises of a number of annular layers which are appended, one on top of the other. Different layers may have different expansion factor when exposed to biological fluids.

in use, at least a portion of the naso/orogastric device 100 is inserted through the nasal or oral cavity, passing through the esophagus and terminating in the stomach lumen. For example, when the naso/orogastric device 100 is a feeding naso/orogastric device, the placing of the distal end of the naso/orogastric device 100 in the stomach lumen allows direct delivery of nutrients, microorganisms, water and/or medications to the stomach, via the inner lumen of the naso/orogastric tube 101.

The self expanding element 102, which is optionally placed at the distal segment of the naso/orogastric device 100, just above the lower esophageal sphincter, functions as a stomach seal, for example as shown at FIG. 1D. When backflow of stomach contents, referred to also as gastrointestinal (GI) content, is pushed toward the esophagus, the self expanding element 102 in the expanded state seals, or substantially closes, the stomach-esophagus passage. Optionally, the self expanding element 102 is wetted before the disposing of the device 100 in the trachea so as to reduce it's rigidity and/or to reduce its expansions time.

In use, the backflow of stomach contents is accumulating below the self expanding element 102 when it is in an expanded state. In the expanded state, the self expanding element 102 fills the gap between the naso/orogastric tube 101 and the esophageal walls, preventing from some or all of the backflow of stomach contents to pass from the stomach to the esophagus. Such a self expanding element 102 is passive, allowing sealing or substantially closing off the stomach-esophagus passage without using actuating means.

According to some embodiments of the present invention, the self expanding element 102 is at least partly soaked with a dissolvable material so as to reduce its expansion rate, or any other polymeric material to be used as a sleeve. For example, a gelatin base material or any other dissolvable material that withholds the self expanding element 102 from absorbing the biological fluids when placing the naso/orogastric tube 101 in the esophagus of the patient is applied. In such a manner, the self expanding element 102 remains in a compressed state for a locating period in which the user can easily locating the naso/orogastric tube 101 in the esophagus. The gelatin base material dissolves after a couple of minutes when the naso/orogastric tube 101 is in place in the esophagus 103. During the locating period the operator introduces the naso/orogastric tube easily and comfortably with no excessive friction. After the naso/orogastric tube 101 is in proper position and the compressed self expanding element 102 is in the lower portion of the esophagus, the gelatin dissolves and the self expanding element 102 absorbs the saliva from the surrounding and as an outcome expends.

It should be noted when the self expanding element 102 absorbs fluids, it soften and becomes more elastic. This facilitates the removing thereof.

Optionally, as shown as FIG. 1C, the self expanding element 102 have one or more conduits 110 for conducting saliva or blood therethrough, from the top of the self expanding element 102 to its bottom. The conduits 110 are optionally tubular lumens formed in parallel to the longitudinal axis 111 of the naso/orogastric tube 101. The diameter of the conduits 110 is optionally between about 1 millimeter (mm) and about 4 mm. Optionally, the length of the conduits 110 is at least as long as the length of the self expanding element 102, for example between about 1 centimeter (cm) and 3 cm.

The diameter and length of the conduit(s) 110 assures while a wave of biological fluids that propagate in high energy does not pass therethrough, for example a backflow of GI, saliva or blood which accumulates above the respective self expanding element 102 slowly drips therethrough.

Reference is now made to FIG. 2A which is the naso/orogastric tube 100 described above with a conduit closing element 201 having one or more flaps 203 which is sized and shaped to seal, at least substantially, the conduit(s) 110, according to some embodiments of the present invention. FIG. 2B is a blowup of the self expanding element 102 with the conduit closing element 201 which is placed therebelow.

One end of each flap 203 is optionally swingably coupled on an annular member and/or to the peripheral surface of the naso/orogastric tube 101 and the other end is optionally rounded so as to avoid cutting or scratching the esophagus. As used herein, swingably coupled means hinged and coupled by a flexible joint.

Figure 3:
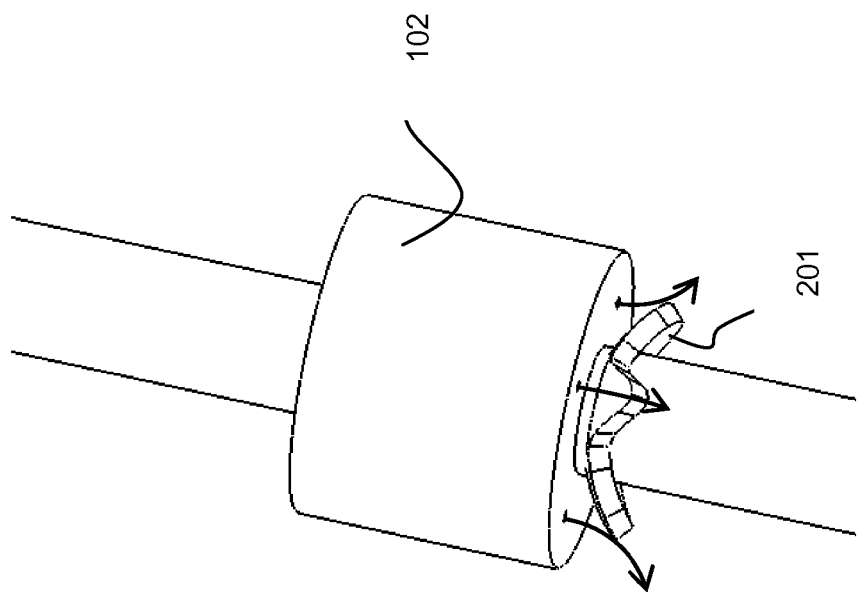
FIG. 3 is the naso/orogastric device depicted in FIG. 2A where the flaps of the conduit closing element are in an open position, according to some embodiments of the present invention.

The flaps 203 may swing relative to the longitudinal axis of the naso/orogastric tube, between a first position substantially in alignment with the naso/orogastric tube 101 and a second position at least about 45° relative to the naso/orogastric tube 101, for example substantially perpendicular to the naso/orogastric tube 101. For example, FIG. 3 depicts the naso/orogastric device 100 where the flaps 203 are in the first position and FIG. 2B depicts the naso/orogastric device 100 where the flaps 203 are in the second position.

Optionally, the flexibility coefficient of the flap decreases toward the peripheral surface of the naso/orogastric tube 101. In such a manner, the flap straightened at the second position, for example substantially perpendicularly to the naso/orogastric tube 101.

Optionally, the flexibility coefficient of the conduit closing element 201 decreases toward the peripheral surface of the conduit closing element 201, for example as an outcome of the arrangement of the flaps 203. Optionally, the conduit closing element 201 is defined as the backflow blocking element in U.S. Provisional Patent Application No. 61/298,944, filed on Jan. 28, 2010, which is incorporated herein by reference.

Figure 4:
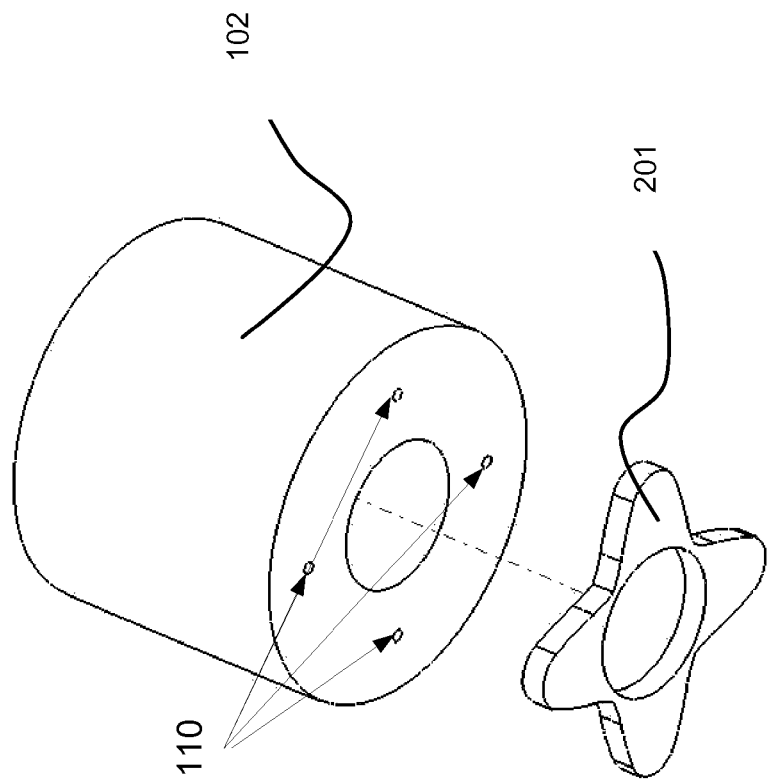
FIG. 4 is a schematic illustration of an exemplary conduit closing element which is set to dynamically seal the conduits of an exemplary self expanding element, according to some embodiments of the present invention.

Optionally, the self expanding element 102 is placed above the flaps 203 so as to limit the swinging movement between the first and second positions. For example, the supporting element may be an annular element having an aperture for receiving the naso/orogastric tube 101 and a width sufficient to limit the movement of the flaps 203. In use, the conduit closing element 201 functions as a dynamic seal of the conduits 110. When backflow of stomach contents is moved toward the pharynx, the flaps 203 swing toward the second position, seal or substantially close off the conduits 110. As the swinging is an outcome of the reflux, the stronger the reflux is, the more tide the blocking operation of the flaps 203 will be achieved. As the seal occurs only when the flaps 203 are pushed, the conduits remain open most of the time, allowing saliva to drip toward the stomach, preventing or delaying their accumulation in the esophagus. In particular, the backflow of stomach contents is accumulating in the space between the flaps 203 and the naso/orogastric tube 101 swings the flaps 203 toward the second position. FIG. 4 depicts an exemplary conduit closing element 201 which is set to dynamically seal the conduits 110 of an exemplary self expanding element, such as 102.

Figure 5C:
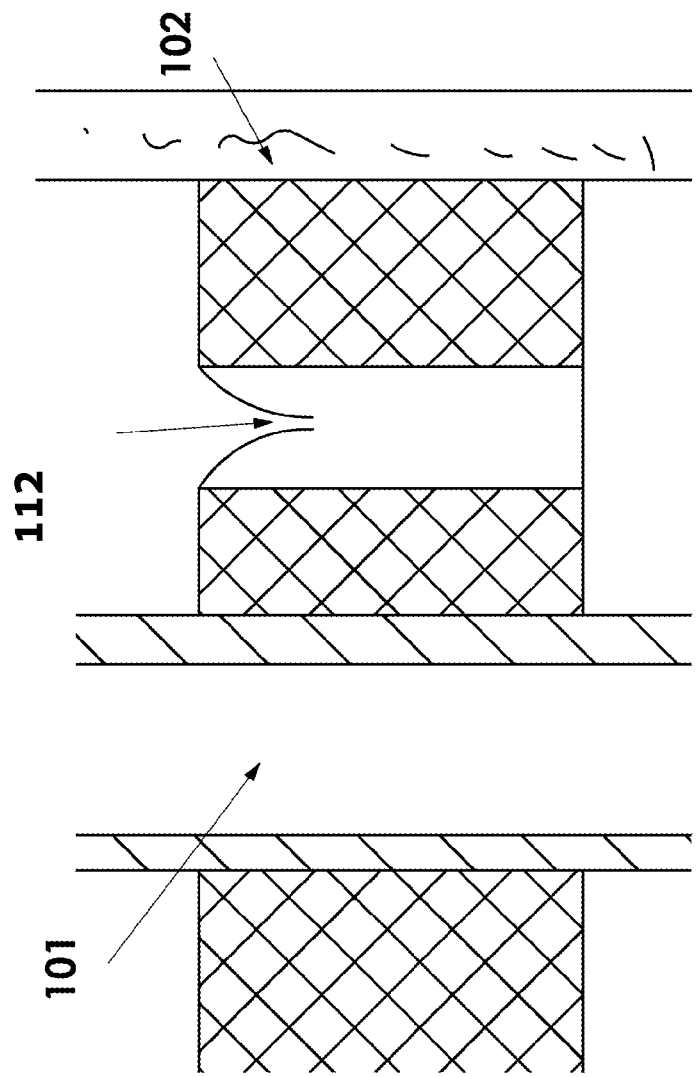
FIG. 5C is a blowup of an exemplary conduit at the cross section of an exemplary backflow blocking element with a unidirectional valve, according to some embodiments of the present invention.

Reference is now made to FIG. 5A, which is a schematic illustration of a naso/orogastric device 500 having a naso/orogastric tube 501 with one or more recesses 502 for conducting saliva or blood in the cross section of a backflow blocking element, such as the aforementioned self expanding element 102, according to some embodiments of the present invention. FIG. 5B is a blowup of an exemplary recess 502 at the cross section of the self expanding element. Optionally, the recess is formed in the outer wall of the naso/orogastric tube 501 and/or in a sheath which is applied thereon and/or set as conduits which are attached to the naso/orogastric tube 501. Optionally, the length of the recess 502 is greater than the length of the self expanding element 102 so that portions thereof are placed above and below the self expanding element 102. In such a manner, saliva and blood accumulated above can pass via the upper segment of the recess (on top of the backflow blocking element 102) toward the lower segment of the recess (below the bottom of the backflow blocking element 102). The passing saliva and blood can now find their way to the stomach and the accumulation thereof in the esophagus, between the self expanding element 102 and the pharynx, is reduces or prevented. Optionally, a unidirectional valve 112 is placed in the recess so as to allow biological fluids from the upper segment of the self expanding element 102, such as saliva and blood, to pass therethrough while blocking biological fluids from the lower segment of the self expanding element 102, such as backflow of stomach contents. Such a unidirectional valve 112 may be added to the aforementioned self expanding element conduits, which are depicted in relation to numeral 110, for example as shown at FIG. 5C.

Figure 6:
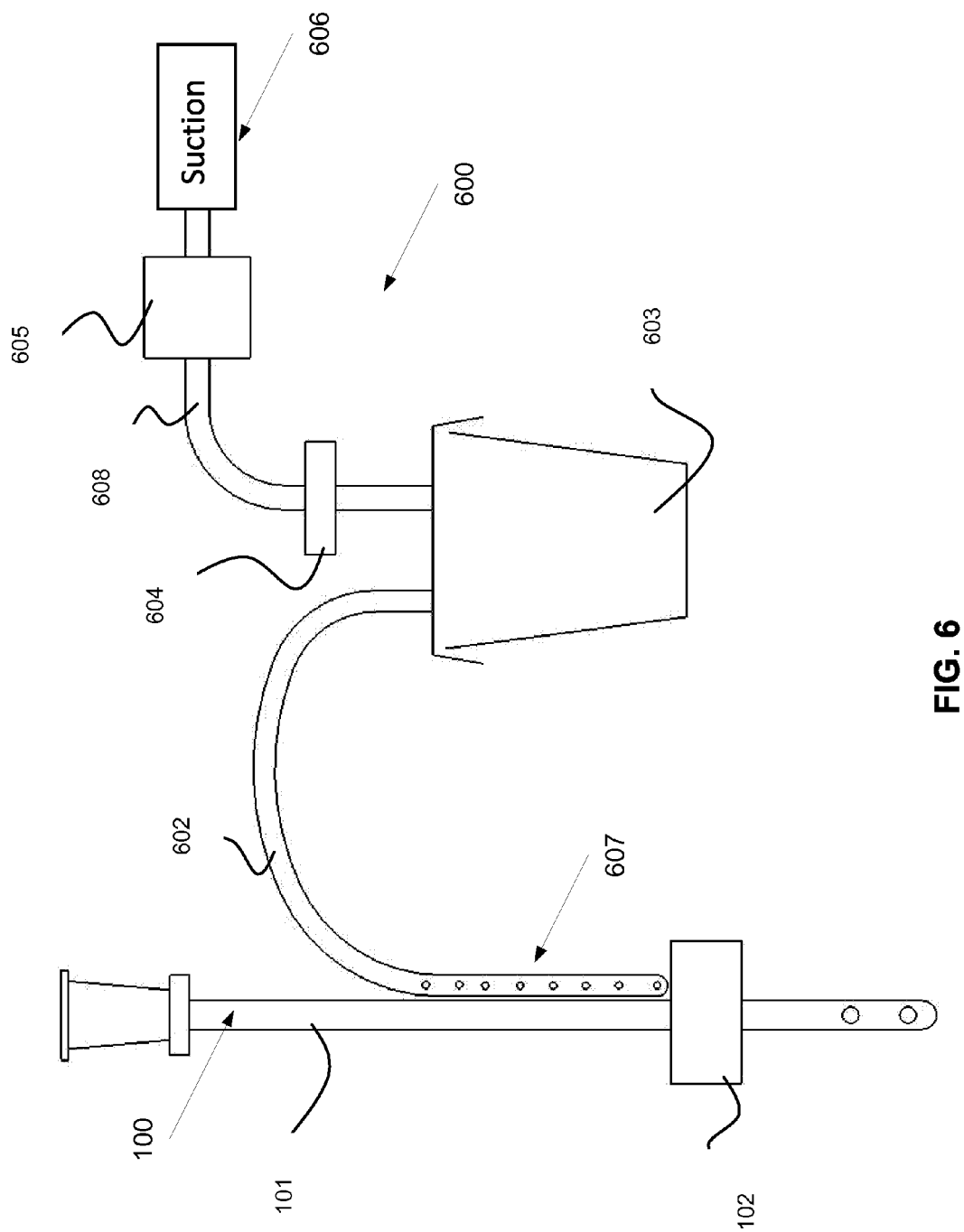
FIG. 6 is a schematic illustration of the naso/orogastric device which is depicted in FIG. 1A with a suction unit for removing content accumulating between the naso/orogastric device and the esophagus walls, according to some embodiments of the present invention.

Reference is now made to FIG. 6, which is a schematic illustration of the naso/orogastric device 100 which is depicted in FIG. 1A with a suction unit 600 for removing content accumulating between the naso/orogastric device 100 and the esophagus walls, above the self expanding element 102, according to some embodiments of the present invention. The suction unit 600 may be set as a separate unit, for example provided part of a kit and/or as a separate product and/or part of the naso/orogastric device 100, for example attached or detachably attached to the naso/orogastric tube 101. The suction unit 600 includes a suction tube 602 having a distal segment with one or more apertures for suction, for example as shown at 607. The suction tube 602 is set to connect operatively to a suction source 606, such as a standard operating room vacuum system or a pump, for example a small scale piston pump or a peristaltic pump. The suction source 606 may be manual, for example syringe-type plunger (not shown). This suction unit 600 allows draining the saliva and/or blood which accumulates, when the naso/orogastric device 100 is inserted into the esophagus of the patient, between the exterior walls of the naso/orogastric tube 101 and the esophagus walls for example every predefined period, manually upon request, and/or upon a signal received from one or more sensors, and the like. Optionally, as depicted in FIG. 6, the suction unit 600 includes a draining tank 603, a filter 604, and/or a suction timing unit 605, connected to the draining tank 603 via a suction source tube 608. In use, the drained biological fluids are accumulated in the draining tank 603. The draining tank 603 is optionally detachably connected to the suction unit 600. In such a manner, the draining tank 603 may be emptied when full and/or from time to time. Optionally, a conduit is connected to the draining tank 603, facilitating a continuous emptying thereof. The filter 604 filters the fluids which are drained toward the suction source 606, preventing from the plugging thereof by the drained saliva and blood. Optionally, the suction timing unit 605 is set to open a valve. The opening of the valve allows the applying of a suction force that drains, or substantially drains, the accumulated saliva and/or blood. The suction timing unit 605 may be set to open the valve every predefined idle period, for example every minute, 5 minutes, 10 minutes, 60 minutes, 120 minutes, and/or any intermediate or longer periods for a predefined suction period, for example 10 seconds, 30 seconds, 1 minute, 5 minutes and/or any intermediate or shorter periods.

Figure 7:
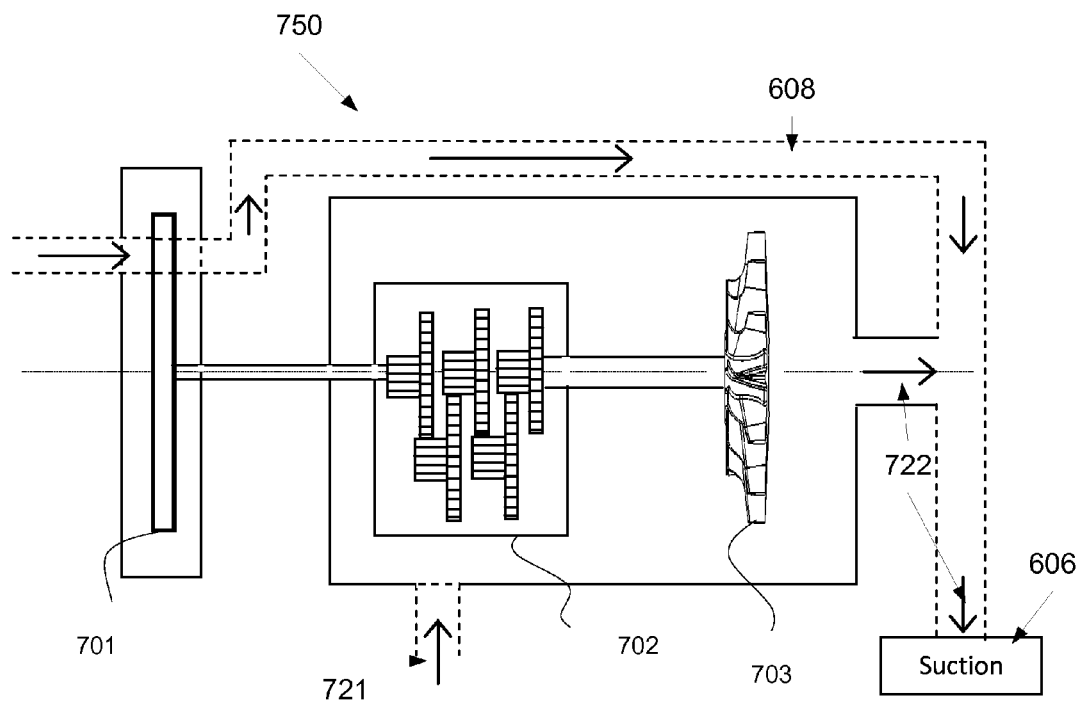
FIG. 7 is a schematic illustration of an exemplary suction timing unit having valve disc controlled by a gear actuated by an actuating unit, according to some embodiments of the present invention.

FIG. 7 is a schematic illustration of an exemplary suction timing unit 750 having valve disc 701 controlled by a gear 702 actuated by an actuating unit 703, such a turbine. In this embodiment the turbine is automatically actuated by the suction force which is applied from the suction source 606. The turbine actuating force route is indicated by numerals 721, 722.

Figure 8:
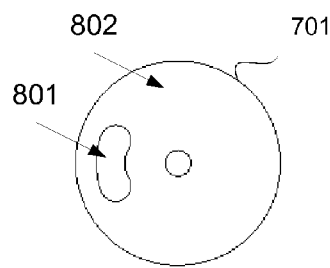
FIG. 8 is a schematic illustration of an exemplary valve disc, according to some embodiments of the present invention.
Figure 9A:
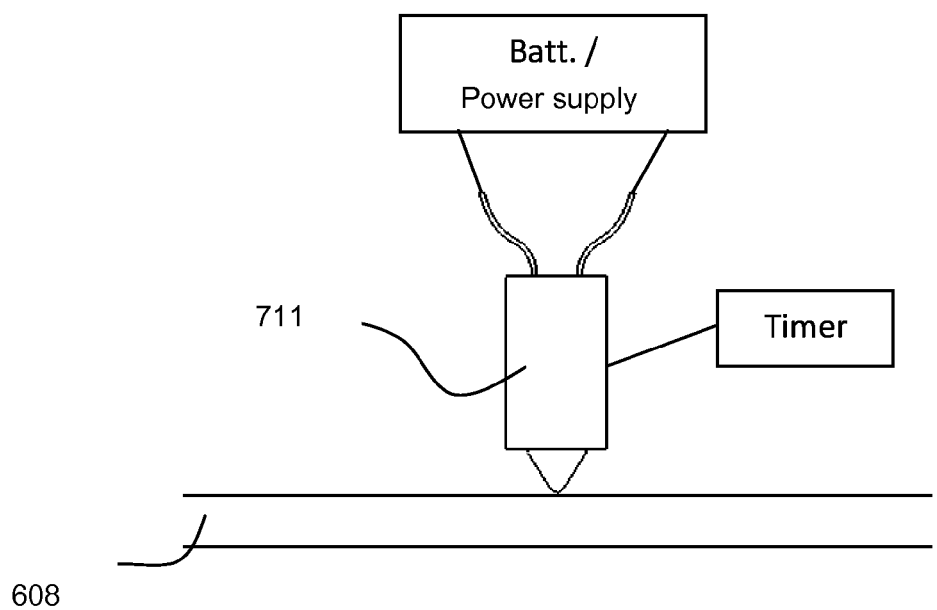
FIGS. 9A and 9B are exemplary schematic illustrations of a solenoid valve controlled by the suction timing unit in open and closed states, according to some embodiments of the present invention.
Figure 9B:
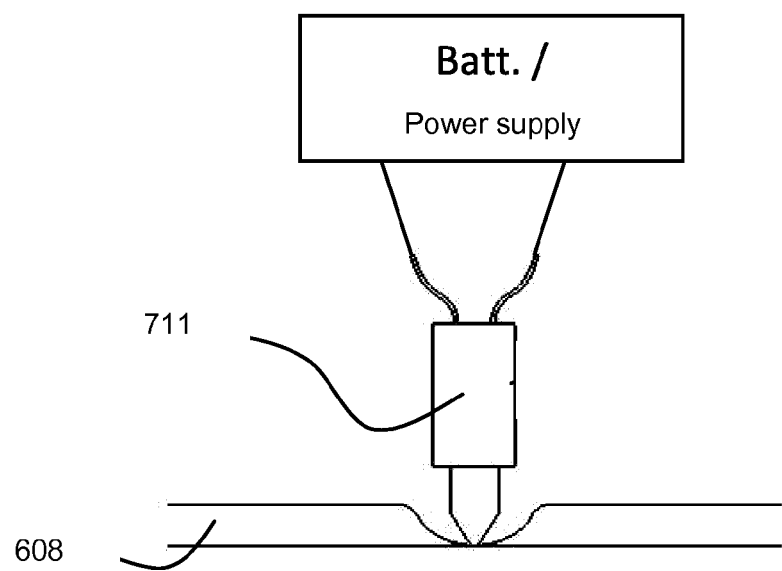
Figure 9C:
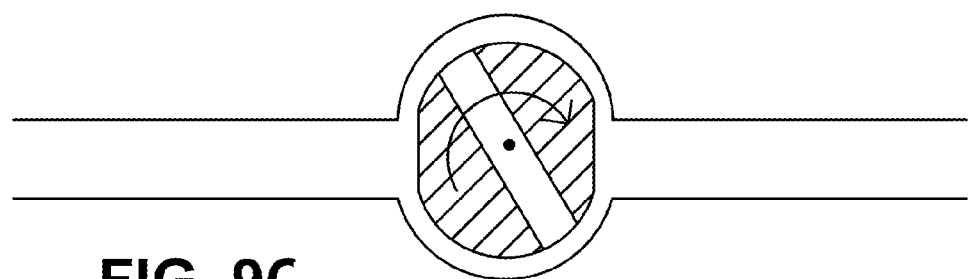
FIGS. 9C and 9D are exemplary schematic illustrations of rotating valves, according to some embodiments of the present invention.
Figure 9D:
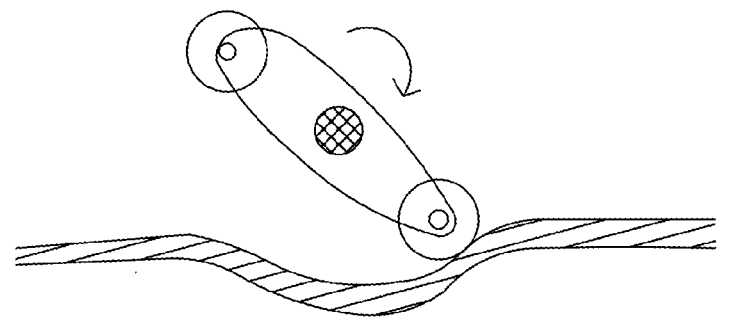

The valve disc 701 is placed in a cross section of a suction force conduit 608 which connects between the tip of the suction source tube 608 and the suction source 606. The gear 702 is set to rotate the valve disc 701, which is optionally shaped with a suction force opening segment 801 and a blocking surface segment 802, as depicted in FIG. 8, in a preset pace. When the suction force opening segment 801 is placed in the cross section of the suction source tube 608, suction force is applied. The preset pace assures a certain predefined idle, namely when the blocking surface segment 802 is placed in the cross section of the suction source tube 608 and a certain predefined suction period, namely when the suction force opening segment 801 is placed in the cross section of the suction source tube 608. FIGS. 9A and 9B are exemplary schematic illustrations of a solenoid valve 711 which is controlled by the suction timing unit 605 in open and closed states, according to some embodiments of the present invention. The solenoid valve 711 is placed to block a cross section of the suction source tube 608 which connects between the tip of the suction tube 602 and the suction source 606. For blocking the suction force, the solenoid applies pressure on the suction source tube 608. For facilitating the suction force, the pressure is released. FIGS. 9C and 9D are exemplary schematic illustrations of rotating valves. In FIG. 9C a plate which rotates in the fluid tube regulates the suction and in FIG. 9D a rotating lever having two wheels attached to its lateral sides is set to apply interchangeably pressure on the tube, moving it between open and closed states, according to some embodiments of the present invention.

Additionally or alternatively, the suction force may be applied according to the reading of one or more sensors, such as impedance sensors. In such an embodiment, the suction timing unit 605 receives the reading of the impedance sensors and operates a suction force valve and/or the suction source 606 accordingly. The suction timing unit 605 may be operated by batteries and/or external AC power. Optionally, the suction timing unit 605 has a plug adapted to the suction source 606 socket of a hospital and/or an ambulance and/or a hospitalization facility.

Figure 10A:
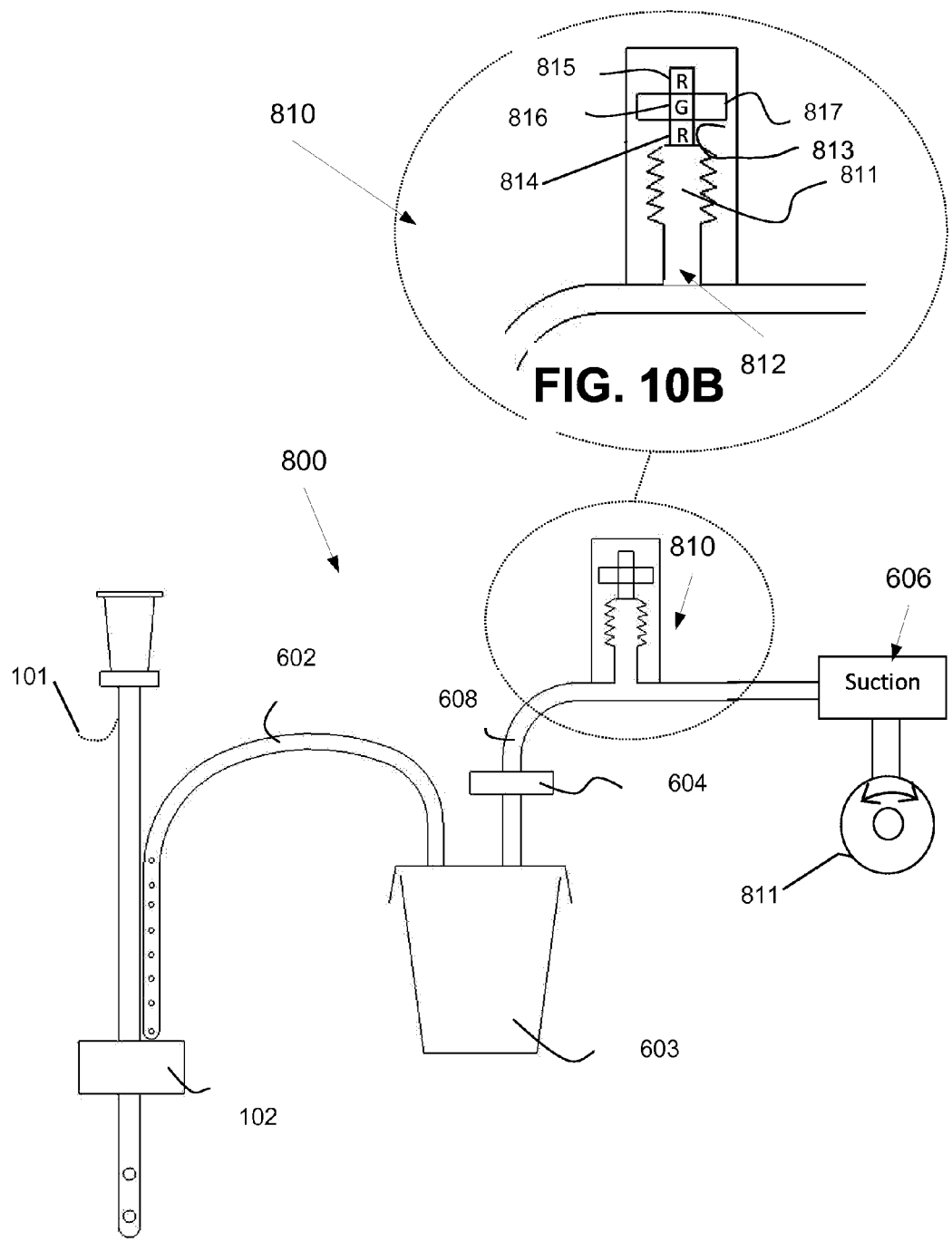
FIG. 10A is a schematic illustration of the naso/orogastric device that is depicted in FIG. 1A with a suction unit for removing content accumulating between the naso/orogastric device and the esophagus walls where the suction unit has a suction timing unit which controls a vacuum regulator and a suction indication unit, according to some embodiments of the present invention.

Reference is now made to FIG. 10A, which is a schematic illustration of the naso/orogastric device 100 that is depicted in FIG. 1A with another suction unit 800 for removing content accumulating between the naso/orogastric device 100 and the esophagus walls, above the self expanding element 102, according to some embodiments of the present invention. In this embodiment, the suction unit 800 has a suction timing unit which controls a vacuum regulator 811 to regulate the suction power according to readings of one or more sensors and/or periodically, for example as described above. Optionally, the suction unit 800 further includes a suction indication unit 810, optionally mechanical, for example as depicted in FIG. 10A and in the blowup of the suction indication unit 810 which is depicted in FIG. 10B. The suction indication unit 810 indicates whether a suction force is applied by the suction unit 800 or not. For example, in the embodiment depicted in FIG. 10B, a lower tip 812 of bellow 811 is connected to the suction force conduit 705 of the suction unit 800. The upper tip 813 of the bellow 811 is connected to a sign 814 elevated or lowered according to the suction force in the suction force conduit 608. The change in the elevation can be seen from an indication window 817, optionally made of a transport polymeric material. Optionally, the sign is interchangeably colored with different colors, for example red 815 and green 816, so that while one color indicates a low pressure, the other indicates a high pressure.

Figure 11:
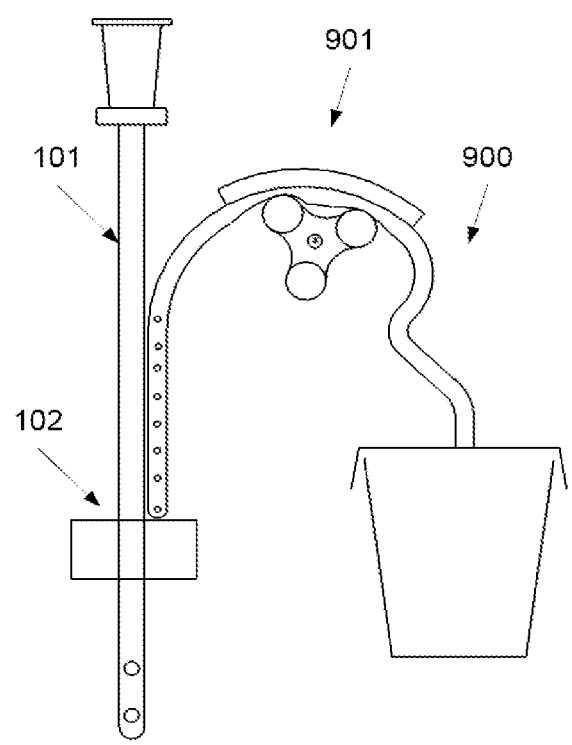
FIG. 11 is a schematic illustration of the naso/orogastric device that is depicted in FIG. 1A with a suction unit which includes a peristaltic pump, according to some embodiments of the present invention.

Reference is now made to FIG. 11, which is a schematic illustration of the naso/orogastric device 100 that is depicted in FIG. 1A with another suction unit 900 for removing content accumulating between the naso/orogastric device 100 and the esophagus walls, above the self expanding element 102, according to some embodiments of the present invention. The suction unit 900 includes a peristaltic pump 901 which changes, in use, the suction force applied in the esophagus. The peristaltic pump 901 is optionally built in and may be operated by the suction timing unit 605, periodically and/or according to the readings of sensors and/or upon request, for example when the user operates it.

Figure 12:
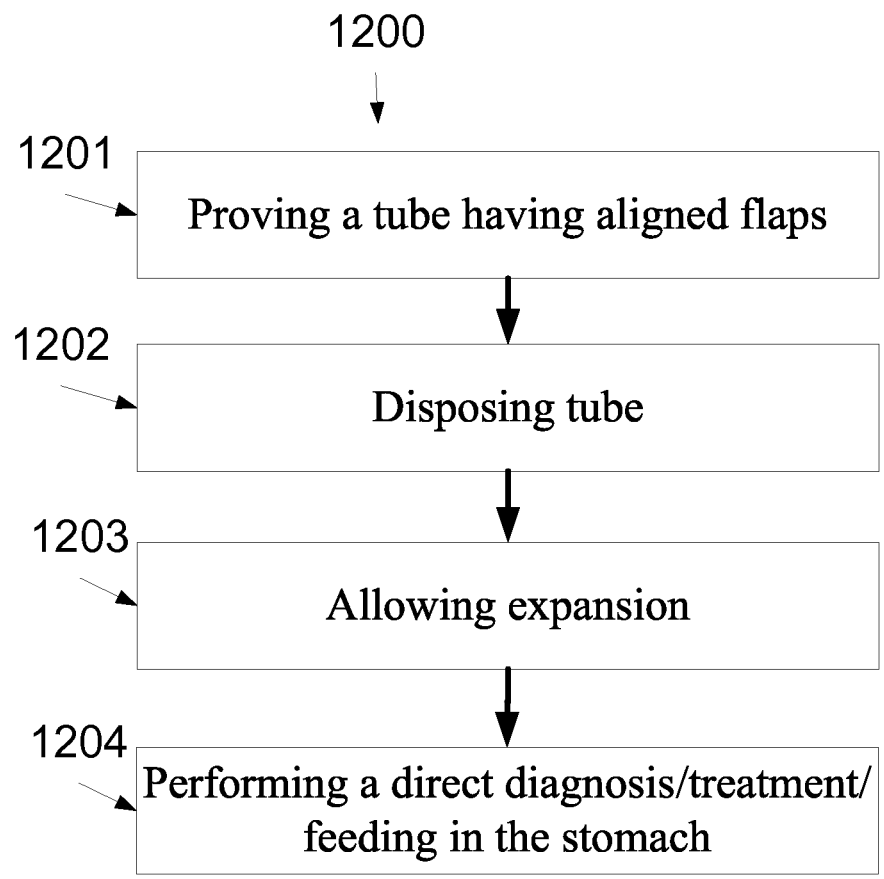
FIG. 12 is a flowchart of a method of in stomach treatment and/or diagnosis, according to some embodiments of the present invention.

Reference is now also made to FIG. 12, which is a flowchart of a method 1200 of in stomach treatment and/or diagnosis, according to some embodiments of the present invention. First, as shown at 1201, a naso/orogastric tube, such as 101, having an inner lumen is provided. The naso/orogastric tube may have an inner lumen for delivering nutrients, microorganisms, water and/or medication and/or one or more GI diagnostical sensors, such as pH sensors, image sensors, fluid sensors, and the like. One or more self expanding elements 102, as shown at FIG. 1A, are circularly coupled to the peripheral surface of the naso/orogastric tube 101. The self expanding elements 102 are in a compress state, for example as described above. For example, the self expanding elements 102 are made of PVA which is soaked with gelatin based material for decrease the biological fluid absorption rate.

Now, as shown at 1202, the naso/orogastric tube is disposed within the esophagus so that a distal end thereof is in the stomach lumen of a patient, for example as shown at FIG. 1D. This allows the self expanding elements 102 to expend, for example as described above and shown at 1203. The expansion forms an annular element around the naso/orogastric tube 101 that seals or substantially closes the esophagus, for example as described above. As described above, the self expanding element 102, is optionally located above the esophageal sphincter and expands to block backflow by sealing or substantially closing off the stomach-esophagus passage. Now, as shown at 1204, the naso/orogastric tube 101 may be used for directly performing a diagnostic procedure and/or a treatment in the stomach lumen. For example, the naso/orogastric tube 101 is a feeding tube that delivers nutrients, microorganisms, water and/or medications via said inner lumen.

It is expected that during the life of a patent maturing from this application many relevant devices and methods will be developed and the scope of the term sensor is intended to include all such new technologies a priori.

As used herein the term "about" refers to ±10.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of at least one of performing a naso/orogastric tube feeding procedure, comprising:
providing a naso/orogastric tube having an inner lumen and at least one self expanding element disposed around a peripheral surface thereof, said at least one self expanding element made of biocompatible porous material and having a first thickness in a compressed state and a second thickness in an expanded state, said at least one self expanding element switching from said compressed state to said expanded state when absorbing biological fluids of a patient within an esophagus;
disposing said naso/orogastric tube within the esophagus so that during the naso/orogastric tube feeding procedure which is held using said naso/orogastric tube, a distal segment of said naso/orogastric tube is in an esophagus lumen of said patient and said at least one self expanding element is disposed above a lower esophageal sphincter of said patient;
allowing said at least one self expanding element to absorb said biological fluids of said patient so as to change from said compressed state to said expanded state in said esophagus lumen; and
using said inner lumen for performing the naso/orogastric tube feeding procedure;
when said at least one self expanding element is within the esophagus in said expanded state, said biocompatible porous material is in contact with esophageal walls of the esophagus.

2. The method of claim 1,
wherein said self expanding element soften and becomes more elastic when absorbing biological fluids of said patient within the esophagus and switching from said compressed state to said expanded state.

3. The method of claim 2, wherein said at least one self expanding element is circularly disposed around said peripheral surface.

4. The method of claim 2, further comprising drawing biological fluids accumulated above said at least one self expanding element.

5. The method of claim 1, wherein said at least one self expanding element having at least one of a disc shaped structure around said naso/orogastric tube when in said expanded state and at least one of compressed cellulose and Polyvinyl acetate (PVA).

6. The method of claim 1, wherein the said first thickness is at least ten folds thinner than said second thickness.

7. The method of claim 1, wherein said at least one self expanding element is at least partly soaked with a dissolvable material.

8. The method of claim 1, wherein said at least one self expanding element having at least one conduit for conducting biological fluids from a top of said at least one self expanding element to a bottom of said at least one self expanding element.

9. The method of claim 8, further comprising at least one conduit closing element having a closed state for substantially sealing said at least one conduit and an open state for substantially unsealing said at least one conduit.

10. The method of claim 9, wherein said at least one conduit closing element having at least one flap, each said flap being swingably coupled on a peripheral surface of said naso/orogastric tube so that said at least one flap swings relative to said naso/orogastric tube, said at least one flap swinging between said closed state and said open state.

11. The method of claim 1, wherein said naso/orogastric tube having at least one of a recess and conduits for conducting biological fluids from a top of said at least one self expanding element to a bottom of said at least one self expanding element.

12. The method of claim 11, further comprising a unidirectional valve disposed in a lumen of said at least one of said recess and said conduit.

13. The method of claim 1, further comprising applying a suction force for drawing biological fluids accumulated above said at least one self expanding element.

14. The method of claim 13, wherein said suction force is transmitted from an external source to a space above said at least one self expanding element, in proximity to said naso/orogastric tube.

15. The method of claim 13, further comprising detecting at least one of a presence and an absence of biological fluids above said at least one self expanding element, in proximity to said naso/orogastric tube, said applying is held according to at least one of said presence and said absence.

16. The method of claim 13, further comprising setting an interval for said applying.

17. The method of claim 13, further comprising indicating whether said suction force is applied.

\* \* \* \* \*